United States Patent [19]
Friedel et al.

[11] Patent Number: 5,750,548
[45] Date of Patent: May 12, 1998

[54] 1-[N-(HALO-3-PYRIDYLMETHYL)]-N-METHYLAMINO-1-ALKLAMINO-2-NITROETHYLENE DERIVATIVES FOR CONTROLLING FLEAS IN DOMESTIC ANIMALS

[75] Inventors: Thomas Friedel, East Blaxland, Australia; Eric William Moyses, Basel, Switzerland; Olivier Tinembart, Delémont, Switzerland; Peter Maienfisch, Rodersdorf, Switzerland; Laurenz Gsell, Basel, Switzerland

[73] Assignee: Novartis Corp., Summit, N.J.

[21] Appl. No.: 639,375

[22] Filed: Apr. 29, 1996

Related U.S. Application Data

[63] Continuation of Ser. No. 443,943, filed as PCT/EP92/01161 May 23, 1992, abandoned.

[51] Int. Cl.$^6$ .......................... C07D 213/36; A01N 43/40
[52] U.S. Cl. .......................... 514/357; 546/334; 424/408
[58] Field of Search .............. 546/332; 424/408; 574/357

[56] References Cited

U.S. PATENT DOCUMENTS

| | | | |
|---|---|---|---|
| 4,973,589 | 11/1990 | Barnett et al. | 514/245 |
| 5,049,571 | 9/1991 | Gsell | 514/345 |

FOREIGN PATENT DOCUMENTS

| | | | |
|---|---|---|---|
| 0255803 | 2/1988 | European Pat. Off. | 514/345 |
| 0302389 | 2/1989 | European Pat. Off. | 514/345 |
| 0302833 | 2/1989 | European Pat. Off. | 514/345 |
| 0375907 | 7/1990 | European Pat. Off. | 514/345 |

*Primary Examiner*—Zinna Northington Davis
*Attorney, Agent, or Firm*—Gabriel Lopez

[57] ABSTRACT

The compounds of formula I are described

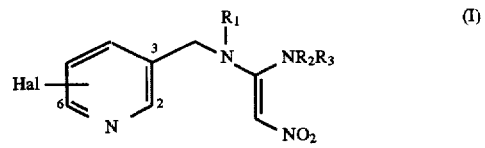

wherein
Hal is halogen, such as fluorine, chlorine, bromine or iodine;
$R_1$ is hydrogen, $C_1$–$C_6$alkyl or $C_3$–$C_7$cycloalkyl;
$R_2$ is hydrogen, $C_1$–$C_6$alkyl or $C_3$–$C_7$cycloalkyl, and
$R_3$ is hydrogen or $C_1$–$C_6$alkyl.

for use in a method of controlling fleas in domestic animals, especially in dogs and cats, wherein systemic administration is preferred. The compounds of formula I are administered in an amount effective against fleas via the digestive tract or via the blood of the host animal and thus systemically to the domestic animal, especially the dog or the cat.

22 Claims, No Drawings

1-[N-(HALO-3-PYRIDYLMETHYL)]-N-METHYLAMINO-1-ALKLAMINO-2-NITROETHYLENE DERIVATIVES FOR CONTROLLING FLEAS IN DOMESTIC ANIMALS

This application is a continuation, of application Ser. No. 08/443,943, filed May 18, 1995, now abandoned, which is a 371 of International application No. PCT/EP 92/01161, filed on May 23, 1992, (U.S. application Ser. No. 08/190,014, 35 USC 371 date of Jan. 24, 1994).

The present invention relates to 1-[N-(halo-3-pyridylmethyl)]-N-methylamino- 1-alkylamino-2-nitroethylene derivatives of the following formula I for use in a method of controlling fleas in domestic animals, especially in dogs and cats, wherein systemic administration is preferred. The invention relates also to a method of inhibiting the infestation of dogs and cats by fleas which comprises the systemic administration of the said compound, in an amount effective against fleas, to the said domestic animal, for example the dog or the cat, by way of the digestive tract or the blood of the host animal.

The 1-[N-(halo-3-pyridylmethyl)]-N-methylamino-1-alkylamino-2-nitroethylene derivatives mentioned in the introduction have the following chemical structure of formula I:

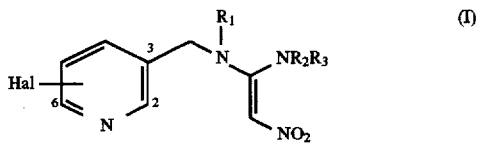

wherein

Hal is halogen, such as fluorine, chlorine, bromine or iodine;

$R_1$ is hydrogen, $C_1$–$C_6$alkyl or $C_3$–$C_7$Cycloalkyl;

$R_2$ is hydrogen, $C_1$–$C_6$alkyl or $C_3$–$C_7$cycloalkyl, and $R_3$ is hydrogen or $C_1$–$C_6$alkyl.

Owing to their pronounced activity against fleas, preference is given within the scope of formula I to the following subgroups:

Group a: Compounds of formula I wherein Hal is in the 6-position. Special preference is given to such compounds wherein Hal is fluorine, chlorine or bromine, especially chlorine.

Group b: Compounds of formula I wherein $R_1$ is hydrogen, $C_1$–$C_3$alkyl or $C_3$–$C_6$cycloalkyl, preferably hydrogen, methyl or ethyl or cyclopropyl, especially ethyl.

Group c: Compounds of formula I wherein $R_2$ is $C_1$–$C_3$alkyl or cyclopropyl, especially methyl.

Group d: Compounds of formula I wherein Hal is halogen, such as fluorine, chlorine, bromine or iodine; $R_1$ is hydrogen, methyl, $C_3$–$C_6$alkyl or $C_3$–$C_7$cycloalkyl and $R_2$ is hydrogen or $C_1$–$C_6$alkyl.

Within groups (a) to (d) preference is given above all to those compounds wherein $R_3$ is hydrogen.

Owing to its pronounced systemic activity against fleas, special preference is given to the following compound:

1-[N-(6-chloro-3-pyridylmethyl)]-N-ethylamino-1-methylamino-2-nitroethylene, and also to its immediate homologues.

Within the scope of the present invention, depending on the number of carbon atoms indicated, the term "alkyl" is to be understood as meaning, for example, the following straight-chained and branched groups: methyl, ethyl, n-propyl, isopropyl, n-butyl, sec-butyl, tert-butyl, isobutyl, etc.. Here and hereinafter, Hal is to be understood as being fluorine, chlorine, bromine or iodine, preferably fluorine, chlorine or bromine, but especially chlorine. Depending on the number of carbon atoms indicated, cycloalkyl by itself or as part of a substituent is cyclopropyl, cyclobutyl, cyclopentyl, cyclohexyl, etc., cyclopropyl being especially preferred.

Compounds of the structural type falling within the scope of formula I, including processes for their preparation, are described in EP-0 302 389. The compounds of formula I can be prepared in accordance with the methods disclosed in EP-0 302 389 or analogously to the compounds described therein. That publication discloses a broad class of compounds of which the above representatives constitute only a selected subgroup, although they do not appear therein as a group. The class of compounds disclosed in EP-0 302 389 is described as insecticidal and acaricidal. Plant-destructive insects and mites are given as the preferred area of application. There is no reference to activity against fleas.

EP-0 302 833 likewise discloses a group of compounds which are structurally similar to those of the above formula I or which to some extent overlap structurally therewith. The essential structural difference between the compounds specifically disclosed and those of formula I is that the former have an unsubstituted pyridyl group, whereas the compounds of formula I are mono-halogenated at the pyridyl radical. The compounds disclosed in EP-0 302 833 are said to be valuable active ingredients in pest control, while being well tolerated by warm-blooded animals and plants, and to be suitable for controlling pests in and on animals and plants. Among the animal-injurious insects, specific reference is made to the order Siphonaptera (fleas).

It has now been found, surprisingly, that in the case of the compounds of the above formula I, the introduction of a halogen atom into the pyridyl radical brings about quite unexpected and significantly increased activity against fleas. That is very clear from a comparison of the principal compound according to the invention and the structurally most similar compound from the prior art. The relevant comparison data are given below in the Biological Examples.

The outstanding activity against fleas exhibited by the compounds of formula I is of such significance because the infestation by fleas of domestic animals and pets, especially of dogs and cats, is a problem for vets and animal owners alike to which there is still no adequate solution.

Owing to the complicated life cycle of the flea, none of the known methods of controlling these extremely troublesome parasites, which not only transmit diseases but are also the cause of unpleasant allergies, is totally satisfactory, especially since most of the known methods of control are based on the application of the active compound to the habitat of the various flea stages. As a result of the complex life cycle of the flea, however, that procedure is very laborious and cannot, in practice, cover all of the habitats, and is accordingly unreliable.

For example, control aimed at treating the adult fleas in the fur, which is generally effected by applying an anti-flea composition to the fur of the host animal, takes no account at all of the various juvenile stages of the fleas, which live not only in the fur of the animal, but also mainly on the floor, on carpets, on the animal's sleeping place, on chairs, in the garden and in all the other places with which the infested animal comes into contact. Adult cat and dog fleas (*Ctenocephalides felis* and *C. canis*) normally live in the fur of the host cat or host dog. They live on the blood of the host animal and lay their eggs in its fur. Since those eggs are not self-adhering, however, they generally soon fall off and can be found on the floor, on carpets, in the dog's or cat's basket, on the chairs used by the animal, in the garden, in the yard, etc..

That means that the whole of the pets' living area is contaminated with flea eggs, from which the larvae develop within two days. The larvae have three distinct stages of development, each of which lasts three days. In the final stage the larva spins its cocoon and becomes a pupa. Under favourable conditions, i.e. at 33° C. and a relative humidity of 65%, the metamorphosis from egg to pupa takes place in about 8 to 10 days. After about another 8 days the young, fully-formed fleas develop in the cocoons that are still lying on the floor, the carpets, the sleeping places, the chairs, etc.. The young adult fleas remain there until they sense the presence of an acceptable host animal, then they hatch from their cocoons and attempt to jump onto the host animal. Thus it takes at least three weeks for an egg to develop into a young adult flea that is capable of reinfesting the host animal.

The young flea may, however, remain in its cocoon for months, possibly for up to a year. On the other hand, under less favourable conditions the development from egg to young adult flea may take from 4 to 5 months. To reach sexual maturity, fleas require blood as food in order to be able to reproduce, and that blood must be from the appropriate host animal. It is normally obtained from the excreta of the adult fleas living on the host animal. Those excreta contain large amounts of undigested blood.

That long life cycle, which proceeds separately from the host animal, has a significant influence on the successful control of fleas on the host animal.

Only when the fleas in the fur of the host animal can be successfully controlled very quickly, i.e. when all the adult fleas are killed within a very short time with a suitable active ingredient, is the cat or the dog protected against the risk of reinfestation by newly hatched young fleas from its living space.

Flea infestation of dogs and cats has unpleasant consequences not only for the animal to be treated but also for the animal's owner. Such drawbacks lead, for example, to local irritation or troublesome itching and often result in intense scratching. A large number of the animals become allergic to the excreta of the fleas, which leads to very itchy and crusty skin changes around the sites of the bites on the animal's body. Those skin changes normally have a diameter of approximately 3 mm or more and often make the animal prone to biting and cause it to scratch, leading to loss of fur in places.

Furthermore, flea-infested animals are constantly exposed to the risk of infestation by dipylidium, a species of tape worm, which is transmitted by fleas.

Flea infestation is not only extremely troublesome for the affected animal, but also has unpleasant consequences for the animal's owner, since it will eventually become evident to him from the unusual behaviour of his pet that it is ill and suffering and that he must help it. What is more, it can become unpleasant for the animal's owner if he gives up keeping his infested animal, or if it dies or is removed temporarily from its usual environment, since in the event of the prolonged absence of a suitable host animal, the newly hatched fleas on the floor will be forced to infest the human, although they are unable to live on human blood as their only source of food. Even when the dog or the cat is present, the animal's owner can still be bitten by the fleas.

In addition, dog and cat fleas, or their excreta, can lead to allergy-like skin disorders in some people, which in many cases means that the pet must be given up. The desire for effective control of fleas in dogs and cats has therefore existed for centuries.

A number of conventional methods of control are known, but they have various disadvantages. If, for example, flea combs surface-coded with an insecticide are used, the animal's owner has no alternative but to comb the animal intensively and often which, depending on the size of the animal, may take from a few minutes to an hour and will not be accepted patiently by every animal. However, not every animal owner is prepared to devote the time to this. The use of corresponding anti-flea shampoos is often unsuccessful, since most cats, and also many dogs, can be bathed, if at all, only by force, with the result that water and active ingredient are spilt and have to be cleared up. In addition, the effect of such a bath treatment lasts about a week at most, and the laborious procedure has to be repeated. The same or very similar problems can be expected with the use of dips or rinses. The use of dusting powders is generally also not accepted by the animal without resistance, since it takes several minutes to treat the whole surface of the fur uniformly, and some of the dust will inevitably get into the mouth, nose and eyes of the animal. Even with careful application, it cannot be ensured that the animal and the human will not inhale any powder. It is virtually inevitable that the human will also come into contact with the composition to a greater or lesser extent.

When using sprays, many people may be unpleasantly surprised to find that most animals, especially cats, run away or react aggressively at the mere sound of the spray. In addition, sprays also have all the disadvantages listed for dusting powders, added to which they become even more finely dispersed in the atmosphere and are therefore inhaled by human and animal. Fleas are frequently controlled by means of so-called flea collars, which ensure good effectiveness temporarily. This treatment has a certain weakness, owing especially to its locally very limited area of application. Although the killing action in the region of the neck and chest is generally 100%, more remote parts of the body are scarcely affected. In addition, those collars are active for a limited time. Furthermore, many of the collars are unattractive and may annoy the animal. It is also possible nowadays to buy medallions, which can be hung from conventional collars and are supposed to be effective. Although they are attractive in appearance, the action of those medallions is unsatisfactory, since they have inadequate contact with the fur. Some anti-flea organophosphorus compounds are also available as spot-on formulations and are thus applied to a locally limited area of the fur. They generally have good short-term activity against adult fleas, but the compositions used often have toxic properties that present problems. Some organophosphorus compounds have also been administered orally, but they are subject to strict safety restrictions and must on no account be administered simultaneously with other organophosphorus compounds.

Overall it may be said that the conventional methods, which seek to kill the adult flea, produce such unsatisfactory results chiefly because they depend on the patience and the skill of the user when handling the infested host animal. The success of the current compositions stands and falls with the frequency and thoroughness with which the user, normally the animal's owner, applies the active ingredient to the host animal and the thoroughness with which he disinfects the environment in which the host animal lives. The conventional methods are relatively expensive, time-consuming and not especially successful in the long term. In the short term, relief can certainly be obtained with the conventional compositions.

What has hitherto not been adequately taken into account in the case of the conventional methods and compositions is the fact that, owing to the particular life cycle of the flea, dogs and cats are repeatedly reinfested by new fleas, partly because contact with the flea eggs, flea larvae and young adult fleas on the floor and/or in the immediate vicinity of the animal is unavoidable, and partly because many pet animals constantly come into contact with infested members of their own species.

Constantly recurring reinfestation is inadequately prevented by conventional compositions or can be prevented only by the application of large amounts of disinfectant, etc..

It has now been found, surprisingly, that using certain systemic methods of administration and using compounds of formula I as active ingredients, it is possible to eliminate the adult fleas very rapidly and completely and thus to intervene in the complex development cycle of the flea by blocking that cycle. Since those compounds exhibit all of their outstanding anti-flea activity also when they are administered to the host animal systemically, i.e. orally, parenterally, subcutaneously, intramuscularly or intravenously, it is possible, by means of their specific periodic administration, in a simple manner to break the vicious circle of constantly recurring reinfestation described above until all the juvenile stages in the living area of the host animal have died. The fleas are killed and prevented from reproducing, the juvenile stages are prevented from maturing and are no longer able to infest the host animal, so that the living area of dogs and cats can be kept free of fleas for a prolonged period. The only unavoidable source of reinfestation is contact with infested members of the same species and that aspect can of course be excluded one hundred percent only by means of long-term treatment. That residual risk is, however, of minor importance.

It has now been found that by oral administration, parenteral administration or administration by means of an implant, of compounds of formula I in an amount effective against fleas, it is possible for infestation by fleas of domestic animals, such as cats and dogs, to be drastically reduced or completely prevented.

What is astonishing in connection with the present invention, however, is that full activity can be achieved even when an active ingredient is administered to the host animal in relatively low concentrations and reaches its target of the adult flea only by the circuitous route via the gastro-intestinal tract and thus via the blood sucked up by the flea. Since systemic administration of the active ingredient brings about the total mortality of the adult fleas, it is now possible to eradicate the fleas. A combination of this systemic administration of the active ingredient with accompanying measures, for example disinfection of the living area of the host animal, makes it possible to eliminate the flea problem even more rapidly, but even without those accompanying measures the flea population is reduced completely or to an acceptable minimum within a few weeks or at the most months.

The compounds of formula I exhibit activity against juvenile flea stages insofar as flea larvae that hatch from the flea eggs are substantially dependent on the excreta of the adult fleas, since they live on that excrement. However, flea excreta comprise large amounts of undigested blood from the host animal and serve as a source of protein for the developing fleas. Since, however, the compounds of formula I kill the adult fleas very rapidly, the necessary excreta are not available and the juvenile stages are deprived of their nutrient base and therefore die before they reach the adult stage. This is also a decisive contributing factor in the interruption of the complex life cycle of the flea and prevents the host animals from being constantly reinfected in their preferred living area by the eggs, and the larvae hatching therefrom, that are scattered all over it.

The present invention thus has two objects, on the one hand the afore-described method of preventing the reinfestation of domestic animals by fleas, and simultaneously of course the inhibition of the reproduction of fleas.

It is essential to the invention that the compounds of formula I are administered in such a manner that they can be taken up in sufficient amounts by the adult, sucking flea with the blood of the host animal and kill the adult flea rapidly before it can provide sufficient uncontaminated food for the flea larvae by way of its excreta. This is achieved with the compounds of the invention using various forms of administration, for example by administering the formulated active ingredient orally. "Formulated" in this case means, for example, in the form of a powder, a tablet, granules, a capsule, an emulsion or a foam, in microencapsulated form, etc.; the animal need not necessarily be given the composition directly, rather it is advantageously mixed with its food, since that form of administration presents the fewest problems both to the host animal and to the person administering the composition. In addition to customary formulation ingredients, any composition that is to be administered orally may of course comprise further adjuvants that encourage the host animal to take the composition voluntarily, for example suitable odorants and flavourings. Oral administration, being easy to carry out, is preferred according to the invention. A further form of administration is parenteral administration, for example by subcutaneous injection or intravenous injection, or with a long-term composition (depot form) in the form of an implant.

Oral administration includes, for example, the administration of dog and cat food ready mixed with the active ingredient, for example in the form of biscuits or treats, chewable tablets, water-soluble capsules or tablets, in a water-soluble form that can be added to the food in the form of drops or in other forms that can be mixed with the animal food. The implants also include any means that can be introduced into the body of the animal in order to release active ingredient.

Percutaneous forms of administration include, for example, subcutaneous, dermal, intramuscular and even intravenous administration of injectable forms. In addition to the customary syringes with needles, needle-less high-pressure syringe devices, as well as pour-on and spot-on formulations, may be expedient.

By selection of a suitable formulation, it is possible to promote the ability of the active ingredient to penetrate through the living tissue of the animal, and/or to maintain its availability. That is important when, for example, a very sparingly soluble active ingredient is used, the low solubility of which requires means for enhancing solubility, since the animal's body fluid is capable of dissolving only small amounts of active ingredient at a time.

The active ingredient may also be present in a matrix formulation which physically prevents the active ingredient from decomposing and maintains the constant availability of active ingredient. The matrix formulation is injected into the body and remains there as a form of depot from which active ingredient is released continuously. Such matrix formulations are known to a person skilled in the art. They are generally wax-like, semi-solid substances, for example vegetable waxes and polyethylene glycols having a high molecular weight.

A high degree of availability of the active ingredient is also obtained by the introduction of an implant of the active ingredient into the animal. Such implants are widely used in veterinary medicine and often consist of silicone-containing rubber. The active ingredient is dispersed in the solid rubber or is located inside a hollow rubber body. Care must be taken that the active ingredient selected is soluble in the rubber implant, since it is first dissolved in the rubber and then seeps continuously out of the rubber material and into the body fluid of the animal to be treated.

The rate of release of the active ingredient from the implant, and thus the length of time during which the implant exhibits activity, is generally determined by the accuracy of the calibration of the implant (amount of active ingredient in the implant), the environment of the implant and the polymer formulation from which the implant has been produced.

Administration of the active ingredient by means of an implant is a further preferred component of the present invention. Such administration is extremely economical and effective, because a correctly dimensioned implant ensures that the concentration of active ingredient in the tissue of the host animal is constant. It is possible nowadays for implants to be so made and implanted in a simple manner that they are capable of supplying the active ingredient over a period of several months. Once the implant has been made, the animal is not disturbed further, and there is no further need to be concerned about the dose.

The administration of veterinary medicinal additives to animal food is well known in the field of animal health. It is usual first to prepare a so-called premix in which the active ingredient is dispersed in a liquid or is in finely divided form in solid carriers. That premix can normally comprise about 1 to 800 g of compound per kg of premix, depending on the desired final concentration in the food.

It is also known that active ingredients may be hydrolysed or weakened by the constituents of the food. Such active ingredients are routinely formulated in a protective matrix, for example in gelatin, before being added to the premix.

The present invention therefore relates to the object of eliminating the adult fleas on the domestic animal, as well as to preventing the further development of the flea larvae by depriving them of food, which is equivalent to systemic prevention of the reinfection of domestic animals, especially of domestic animals by fleas. This is achieved by administering* to the said host animal orally, parenterally or by means of an implant at least one compound of formula I in an amount effective against fleas.

*Translator's note: "zusetzt" presumably in error for "verabreicht"

The present invention thus also relates to the object of preventing the reproduction of fleas, which comprises making available to fleas as food, by means of the systemic administration of the active ingredient to the host animal, contaminated blood that comprises at least one compound of formula I in an amount effective against fleas. This is most easily achieved by administering to the host animal, in the form of a food additive, a compound of formula I in an amount effective against fleas, and in that way allowing it to reach the fleas living on the host animal.

The compounds of formula I are advantageously administered in a dose of from 0.01 to 800, preferably from 0.1 to 200, especially from 0.5 to 30, mg/kg of body weight of the host animal, oral administration being preferred.

A good dose that can be administered to the host animal regularly is from 0.5 to 100 mg/kg of body weight. Administration is advantageously effected daily or weekly.

The total dose may vary for the same active ingredient from one species of animal to another as well as within a species of animal, since it depends inter alia on the weight and the constitution of the animal.

When used according to the invention, the active ingredient is not normally administered in pure form, but preferably in the form of a composition which comprises in addition to the active ingredient constituents that assist administration, suitable constituents being those that are tolerated by the host animal. It is of course possible, as well as controlling the adult fleas in accordance with the invention, additionally to use conventional methods that control the juvenile flea stages, although the latter is not absolutely essential.

Such compositions to be administered in accordance with the invention generally comprise from 0.1 to 99% by weight, especially from 0.1 to 95% by weight, of a compound of formula I and from 99.9 to 1% by weight, especially from 99.9 to 5% by weight, of a solid or liquid, non-toxic adjuvant, including from 0 to 25% by weight, especially from 0.1 to 25% by weight, of a non-toxic surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as other active ingredients for obtaining special effects.

The materials known from veterinary medicinal practice for oral and parenteral administration and for implants can be used as formulation excipients. Some examples are given below.

Suitable excipients are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatin, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuvants are especially flow conditioners and lubricants, for example silicic acid, talc, stearic acid or salts thereof, such as magnesium or calcium stearate, and/or polyethylene glycol. Dragee cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavourings or pigments may be added to the tablets or dragée coatings, for example for identification purposes or to indicate different doses of active ingredient.

Other orally administrable compositions are dry-filled capsules comprising gelatin, and also soft sealed capsules comprising gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers may also have been added. Preference is given inter alia to capsules that are easily bitten through or swallowed without being chewed.

Suitable for parenteral administration are especially aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilisers.

The compositions of the present invention can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and processing the mixture or granules, if desired or necessary after the addition of suitable excipients, to form tablets or dragée cores.

The following Examples illustrate the invention described above, but do not limit its scope in any way. Temperatures are given in degrees Celsius.

TABLE

Examples of compounds of formula I that can be used in accordance with the invention

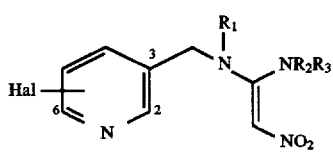

(I)

| Comp. No. | Hal | R₁ | R₂ | R₃ | melting point in °C. |
|---|---|---|---|---|---|
| 1.1 | 6-Cl | CH₃ | CH₃ | H | 87–90 |
| 1.2 | 6-Cl | C₂H₅ | CH₃ | H | yellow oil |
| 1.3 | 6-Cl | CH₃ | C₂H₅ | H | 112–114 |
| 1.4 | 6-Cl | CH₃ | C₃H₇-i | H | 133–135 |
| 1.5 | 6-Cl | CH₃ | C₄—H₉-n | H | |
| 1.6 | 6-Cl | CH₃ | C₄—H₉-t | H | |
| 1.7 | 6-Cl | CH₃ | C₄—H₉-s | H | |
| 1.8 | 6-Cl | CH₃ | C₅—H₉-n | H | |
| 1.9 | 6-Cl | CH₃ | C₆—H₁₃-n | H | |
| 1.10 | 6-F | CH₃ | CH₃ | H | 100–100.5 |
| 1.11 | 5-Br | CH₃ | CH₃ | H | 116–117 |
| 1.12 | 2-Cl | CH₃ | CH₃ | H | 106–113 |
| 1.13 | 6-Cl | C₃H₇-iso | CH₃ | H | |
| 1.14 | 6-Cl | C₄—H₉-n | CH₃ | H | |
| 1.15 | 6-Cl | C₄—H₉-tert | CH₃ | H | |
| 1.16 | 6-Cl | C₄—H₉-sec | CH₃ | H | |
| 1.17 | 6-Cl | C₆—H₁₃-n | CH₃ | H | |
| 1.18 | 6-Cl | cyclopropyl | CH₃ | H | 104–105 |
| 1.19 | 6-Cl | cyclobutyl | CH₃ | H | |
| 1.20 | 6-Cl | cyclopentyl | CH₃ | H | |
| 1.21 | 6-Cl | cyclohexyl | CH₃ | H | |
| 1.22 | 6-Cl | cycloheptyl | CH₃ | H | |
| 1.23 | 6-Cl | H | CH₃ | H | 158–161 |
| 1.24 | 6-Cl | C₂H₅ | H | H | 159–161 |
| 1.25 | 6-Cl | CH₃ | H | H | 202 decomp. |
| 1.26 | 5-Cl | CH₃ | CH₃ | H | |
| 1.27 | 4-Cl | CH₃ | CH₃ | H | |
| 1.28 | 6-Cl | cyclopropyl | C₂H₅ | H | 144–146 |
| 1.29 | 6-F | C₂H₅ | CH₃ | H | oil |
| 1.30 | 6-Br | C₂H₅ | CH₃ | H | 79–80 |
| 1.31 | 6-Cl | H | CH₃ | CH₃ | 97–98 |
| 1.32 | 6-Br | CH₃ | CH₃ | H | 130–131 |
| 1.33 | 6-Cl | CH₃ | CH₃ | CH₃ | 110–112 |
| 1.34 | 6-Cl | H | C₂H₅ | CH₃ | 87–88 |
| 1.35 | 6-Cl | C₃H₇-iso | H | H | resin |
| 1.36 | 6-Cl | H | H | H | 188–190 |
| 1.37 | 6-Cl | C₃H₇-n | H | H | 185–186 |
| 1.38 | 6-Cl | C₃H₇-n | H | CH₃ | 102–103 |
| 1.39 | 6-Cl | C₃H₇-iso | H | CH₃ | 119–120 |

TABLE-continued

Examples of compounds of formula I that can be used in accordance with the invention

| Comp. No. | Hal | R₁ | R₂ | R₃ | melting point in °C. |
|---|---|---|---|---|---|
| 1.40 | 6-Cl | cyclopropyl | H | cyclopropyl | 113–115 |

In the Formulation Examples that follow, the term active ingredient stands for 1-[N-(6-chloro-3-pyridylmethyl)]-N-ethylamino-1-methylamino-2-nitroethylene.

EXAMPLE 1

Tablets comprising 25 mg of active ingredient can be prepared as follows:

| Constituents (for 1000 tablets) | |
|---|---|
| active ingredient | 25.0 g |
| lactose | 100.7 g |
| wheat starch | 7.5 g |
| polyethylene glycol 6000 | 5.0 g |
| talcum | 5.0 g |
| magnesium stearate | 1.8 g |
| demineralised water | q.s. |

Preparation

All the solid ingredients are first forced through a sieve having a mesh size of 0.6 mm. Then the active ingredient, the lactose, the talcum and half the starch are mixed together. The other half of the starch is suspended in 40 ml of water and the suspension is added to a boiling solution of the polyethylene glycol in 100 ml of water. The resulting starch paste is added to the main batch and the mixture is granulated, if necessary with the addition of water. The granules are dried overnight at 35°, forced through a sieve having a mesh size of 1.2 mm, mixed with the magnesium stearate and compressed to form tablets having a diameter of about 6 mm which are concave on both sides.

EXAMPLE 2

Tablets comprising 0.02 g of active ingredient are prepared as follows:

| Composition (for 10 000 tablets) | |
|---|---|
| active ingredient | 200.00 g |
| lactose | 290.80 g |
| potato starch | 274.70 g |
| stearic acid | 10.00 g |
| talcum | 200.00 g |
| magnesium stearate | 2.50 g |
| colloidal silica | 32.00 g |
| ethanol | q.s. |

A mixture of the active ingredient, the lactose and 194.70 g of potato starch is moistened with an ethanolic solution of the stearic acid and granulated through a sieve. After drying, the remaining potato starch, the talcum, the magnesium stearate and the colloidal silica are mixed in and the mixture is compressed to form tablets each weighing 0.1 g, which may, if desired, be provided with dividing notches for finer adaptation of the dose.

EXAMPLE 3

Capsules comprising 0.025 g of active ingredient can be prepared as follows:

| Composition (for 1000 capsules) | |
| --- | --- |
| active ingredient | 25.00 g |
| lactose | 249.80 g |
| gelatin | 2.00 g |
| corn starch | 10.00 g |
| talcum | 15.00 g |
| water | q.s. |

The active ingredient is mixed with the lactose, the mixture is moistened uniformly with an aqueous solution of the gelatin and granulated through a sieve having a mesh size of 1.2–1.5 mm. The granules are mixed with the dried corn starch and the talcum and introduced in 300 mg portions into hard gelatin capsules (size 1).

EXAMPLE 4

Premix (food additive)

0.25 part by weight of active ingredient and 4.75 parts by weight of secondary calcium phosphate, alumina, Aerosil, carbonate or chalk are mixed until homogeneous with 95 parts by weight of an animal food.

EXAMPLE 5

Premix (food additive)

0.40 part by weight of active ingredient and 5.00 parts by weight of Aerosil/chalk (1:1) are mixed until homogeneous with 94.6 parts by weight of a commercial dry food.

EXAMPLE 6

Emulsifiable concentrate 20 parts by weight of active ingredient are mixed with 20 parts by weight of the emulsifier, e.g. a mixture of alkylarylpolyglycol ether with alkylarylpolysulfonates, and with 60 parts by weight of a solvent, until the solution has been completely homogenised. Emulsions of the desired concentration are obtained by dilution with water.

EXAMPLE 7

Solutions (e.g. for use as a drink additive)

15 percent by weight active ingredient in 2,2-dimethyl-4-hydroxymethyl-1,3-dioxolane, 10 percent by weight active ingredient in diethylene glycol monoethyl ether, 10 percent by weight in polyethylene glycol 300, and 5 percent by weight in glycerol.

EXAMPLE 8

Soluble powder 25 parts by weight of active ingredient 1 part by weight of sodium lauryl sulfate, 3 parts by weight of colloidal silica gel, and 71 parts by weight of urea.

The ingredients are mixed together and ground with one another until homogeneous.

Other biologically active compounds or adjuvants that are neutral towards the active ingredients and that have no adverse effect on the host animal to be treated, as well as mineral salts or vitamins, can be added to the compositions described.

Biological Examples

EXAMPLE 9

Comparison test of action against *Ctenocephalides felis* (cat flea)

In accordance with the following protocol, both the active ingredient according to the invention, 1-[N-(6-chloro-3-pyridylmethyl)]-N-ethylamino-1-methylamino-2-nitroethylene having the chemical structure:

Compound (A) of the invention

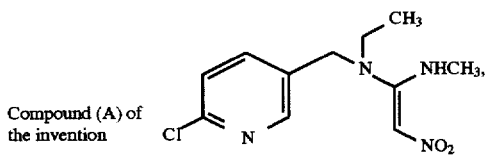

and the structurally most similar compound mentioned in EP-0 302 833, of the formula:

Compound (B) of the prior art

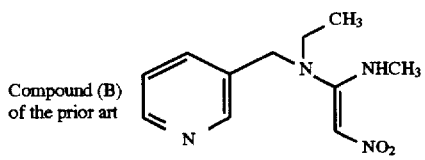

are tested for comparison purposes against an untreated control group of fleas.

Test protocol 20 adult fleas of the species *Ctenocephalides felis* are introduced into a flat round cage closed off at both ends with gauze. A vessel sealed at the bottom with a parafilm membrane is then placed on the cage. The vessel contains blood comprising 1.0 ppm of active ingredient and is heated to a constant temperature of 37° C. The fleas take up the blood through the membrane. Evaluation is effected 24 and 48 hours after the start of the test. The percentage reduction in population (% activity) is determined from a comparison of the number of dead fleas given treated blood with those given untreated blood (control group). 24 hours after treatment the blood is replaced with fresh blood that has likewise been treated and the test is continued with the surviving fleas. The untreated blood for the control group is also replaced after 24 hours.

13
Results

All three groups of fleas [(Control group/untreated blood); (Group A/blood treated with compound A of the invention) and (Group B/blood treated with compound B from the prior art)] begin to take up blood as soon as they are placed in the test apparatus. The behaviour of the control group and of Group B (prior art) remains virtually unchanged over the duration of the test. In contrast, only half an hour after the start of the test the first toxic signs appear in Group A (treatment according to the invention). After 24 hours the following individual results are observed using 2×20 fleas in each case (in % mortality):

| Compound | ppm a.i. | Test 1 | Test 2 | Test 3 | Test 4 |
|---|---|---|---|---|---|
| B | 1.0 | 0% | 5% | 0% | 0% |
| A | 1.0 | 100% | 95% | 95% | 100% |
| Control | 0.0 | 0% | 0% | 0% | 0% |

EXAMPLE 10

In vivo comparison test of the action against *Ctenocephalides felis* (cat flea)

In this comparative test, as in Example 9, compound A of the invention is again tested on cats and compared with the structurally most similar compound B of the prior art.

When other compounds from the Table are tested with the compounds of formula I given by way of example, entirely comparable results are obtained.

Test protocol 6 female domestic cats 1–2 years old and having a body weight of from 3.0 to 4.0 kg are divided into three groups of two animals. One group is already infested with fleas, but remains untreated and serves as control group. One of the other groups receives test compound A and the other receives test compound B, in each case in a dose of 10 mg/kg of a gelatin capsule directly into the back of the throat. Each of the test compounds has been mixed beforehand with lactose 1:1. Immediately after administration of the test compounds the cats are infested with 20 fleas each (16 female and 4 male fleas) in the region of the ridge between the shoulderbones. Further infestation with a further 20 fleas is effected in the case of compound A on days +2, +4 and +6. In the case of the cats treated with compound B and in the case of the comparison group, further infestation with fleas is unnecessary, since all the fleas from the initial infestation have survived.

The flea eggs are collected daily and counted. The number of dead fleas found is also determined daily. The results for the 2 treated groups are compared both with each other and with those for the control group.

Results

The number of dead fleas found and the egg production are shown in the following Tables 1 and 2:

TABLE 1

| | | Number of fleas killed | | | | | | | | | |
|---|---|---|---|---|---|---|---|---|---|---|---|
| Com- | | | | | dead fleas on day . . . | | | | | | |
| pound | Cat no. | 0 | +1 | +2 | +3 | +4 | +5 | +6 | +7 | +8 | +9 |
| A | 325 | 12* | 1 | 0* | 11 | 5* | 0 | 2* | 0 | 0 | 0 |
| | 343 | 9* | 1 | 0* | 8 | 2* | 0 | 2* | 0 | 0 | 0 |
| B | 351 | 0* | 1 | 0 | 0 | 0 | 0 | 0 | 0 | 0 | 0 |
| | 266 | 0* | 0 | 0 | 0 | 0 | 0 | 0 | 0 | 0 | 0 |
| Control | 339 | 0* | 0 | 0 | 0 | 0 | 0 | 0 | 0 | 0 | 0 |
| | 599 | 0* | 0 | 0 | 0 | 0 | 0 | 0 | 0 | 0 | 0 |

*Infestation with 20 fleas

In the case of compound A, only 6 hours after infestation with the first 20 fleas there is 60% mortality. Even on the second day after fresh infestation with a further 20 fleas, a further 55% of the fleas are killed. Not until day 6 does the activity of compound A fall to approximately 10%. In contrast, no significant difference is found between the control group and the group of cats treated with compound B. Compound B proves ineffective and unusable for oral administration against fleas at the low test concentrations.

TABLE 2

| | | Egg production | | | | | | | |
|---|---|---|---|---|---|---|---|---|---|
| Com- | Cat | | | | egg production on day . . . | | | | |
| pound | no. | +2 | +3 | +4 | +5 | +6 | +7 | +8 | +9 |
| A | 325 | 0* | 0 | 0* | 0 | 37* | 233 | 250 | 370 |
| | 343 | 0* | 0 | 0* | 60 | 0* | 186 | 240 | 283 |
| B | 351 | 240 | 306 | 403 | 423 | 350 | 333 | 343 | 290 |
| | 266 | 106 | 266 | 386 | 313 | 286 | 290 | 326 | 303 |
| Control | 339 | 60 | 133 | 186 | 300 | 310 | 313 | 290 | 233 |
| | 599 | 96 | 110 | 156 | 146 | 166 | 116 | 200 | 170 |

*Infestation with 20 fleas

In the group treated with compound A, no flea eggs are found after the first and second infestations with fleas. In the group of cats treated with compound B and in the control group, the female fleas produce the usual number of egos; no significant differences are found.

The comparison test shows that compound A has good systemic activity against adult fleas for a period of about 3–4 days. Compound B, on the other hand, can be classed as completely ineffective at the test dose. It could be neither predicted nor expected that the mono-halogenation of the pyridyl group would bring about such a significant increase in activity as regards the systemic action against fleas.

The compounds for which physical data are given in the Table of compounds that may be used in accordance with the invention exhibit activity against fleas that is comparable with that of compound A of the invention. Especially striking is the outstanding activity of compounds 1.1 to 1.4, 1.10 to 1.12, 1.18, 1.28, 1.29 and 1.36 to 1.40.

What is claimed is:

1. An oral food composition for preventing the infestation of domestic animals by fleas, which comprises, in an amount effective against fleas, a compound of formula I

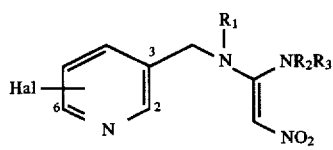

wherein

Hal is halogen;

$R_1$ is hydrogen, $C_1$–$C_6$alkyl, or $C_3$–$C_7$cycloalkyl;

$R_2$ is hydrogen, $C_1$–$C_6$alkyl, or $C_3$–$C_7$cycloalkyl; and $R_3$ is hydrogen or $C_1$–$C_6$alkyl.

2. A composition of claim 1 wherein Hal is fluorine, chlorine, bromine, or iodine.

3. A composition of claim 1 wherein the food is dog or cat food.

4. A method for systemic control of fleas in a domestic animal, which comprises administering to the said domestic animal orally, parenterally, or in the form of an implant, in an amount effective against fleas, a compound of formula I

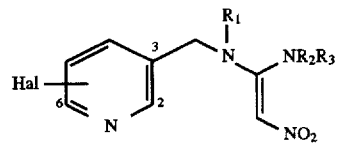

wherein

Hal is halogen;

$R_1$ is hydrogen, $C_1$–$C_6$alkyl, or $C_3$–$C_7$cycloalkyl;

$R_2$ is hydrogen, $C_1$–$C_6$alkyl, or $C_3$–$C_7$cycloalkyl; and $R_3$ is hydrogen or $C_1$–$C_6$alkyl.

5. A method of claim 4 wherein Hal is fluorine, chlorine, bromine, or iodine.

6. A method of claim 4, wherein Hal is in the 6-position and is fluorine, chlorine, or bromine.

7. A method of claim 4, wherein $R_1$ is hydrogen, $C_1$–$C_3$alkyl, or $C_3$–$C_6$cycloalkyl.

8. A method of claim 7 wherein $R_1$ is hydrogen, methyl, or cyclopropyl.

9. A method of claim 4, wherein $R_2$ is $C_1$–$C_3$alkyl or cyclopropyl.

10. A method of claim 9 wherein $R_2$ is methyl.

11. A method of any one of claims 4 to 10, wherein $R_3$ is hydrogen.

12. A method of claim 4, wherein the domestic animal is a dog or a cat.

13. A method of claim 12, further comprising controlling the juvenile flea stages using conventional larvicidal or ovicidal anti-flea compositions.

14. A method of claim 4, which comprises administering orally in regular individual doses a composition comprising a compound of formula I.

15. A method of claim 4, which comprises administering a compound of formula I to the domestic animal in concentrations of from approximately 0.01 mg/kg of body weight to approximately 800 mg/kg of body weight.

16. A method of claim 15, which comprises administering a compound of formula I to the domestic animal in concentrations of from approximately 0.1 mg/kg of body weight to approximately 200 mg/kg of body weight.

17. A method of claim 16, which comprises administering a compound of formula I to the domestic animal in concentrations of from approximately 0.5 mg/kg of body weight to approximately 30 mg/kg of body weight.

18. A method of claim 15, which comprises orally administering a compound of formula I to a cat or a dog.

19. A method of claim 4, which comprises regularly administering a compound of formula I to a cat or a dog in a dose of from 0.5 mg/kg of body weight to approximately 100 mg/kg of body weight.

20. A method of preventing the reproduction of fleas in a domestic animal, which comprises introducing into the blood of the said domestic animal, in an amount effective against fleas, a compound of formula I

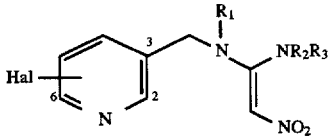

wherein $R_1$ is hydrogen, $C_1$–$C_6$alkyl, or $C_3$–$C_7$cycloalkyl;

$R_2$ is hydrogen, $C_1$–$C_6$alkyl, or $C_3$–$C_7$cycloalkyl; and $R_3$ is hydrogen or $C_1$–$C_6$alkyl.

21. A method of claim 20 wherein Hal is fluorine, chlorine, bromine, or iodine.

22. A method of claim 20 which comprises administering an effective amount of a compound of formula I to a domestic animal with its food and allowing said compound to be taken up by the fleas on the domestic animal with the blood they suck up.

* * * * *

UNITED STATES PATENT AND TRADEMARK OFFICE
CERTIFICATE OF CORRECTION

PATENT NO. : 5,750,548
DATED : May 12, 1998
INVENTOR(S) : Thomas Friedel et al.

It is certified that error appears in the above-identified patent and that said Letters Patent is hereby corrected as shown below:

Title page, left column, Item [63] should read:

-- [63] Continuation of Serial No. 08/443,943, May 18, 1995, abandoned, which is a division of Serial No. 08/190,014, January 24, 1994, abandoned, which is a 371 of PCT/EP92/01161, May 23, 1992 --

Signed and Sealed this

Third Day of August, 1999

Attest:

Q. TODD DICKINSON

*Attesting Officer*    *Acting Commissioner of Patents and Trademarks*